US00PP19995P2

(12) United States Plant Patent
Dümmen

(10) Patent No.: US PP19,995 P2
(45) Date of Patent: May 12, 2009

(54) POINSETTIA PLANT NAMED 'DUEINFINITYWI'

(50) Latin Name: *Euphorbia pulcherrima*
Varietal Denomination: Dueinfinitywi

(75) Inventor: Tobias Dümmen, Rheinberg (DE)

(73) Assignee: Capital Green Investments Ltd., Grand Cayman (KY)

( * ) Notice: Subject to any disclaimer, the term of this patent is extended or adjusted under 35 U.S.C. 154(b) by 0 days.

(21) Appl. No.: 12/070,567

(22) Filed: Feb. 19, 2008

(51) Int. Cl.
*A01H 5/00* (2006.01)

(52) U.S. Cl. ..... Plt./305

(58) Field of Classification Search ..... Plt./304, Plt./305
See application file for complete search history.

(56) References Cited

PUBLICATIONS

UPOV–ROM Plant Variety Database 2008/03, GTI Jouve Retrieval Software, Citation for Euphorbia 'Dueinfinitywi' one page.*

* cited by examiner

*Primary Examiner*—June Hwu
(74) *Attorney, Agent, or Firm*—C. A. Whealy

(57) ABSTRACT

A new and distinct cultivar of Poinsettia plant named 'Dueinfinitywi', characterized by its upright and outwardly spreading plant habit; freely branching habit; early flowering habit; inflorescences with light yellow-colored flower bracts; and excellent post-production longevity.

1 Drawing Sheet

Botanical designation: *Euphorbia pulcherrima.*
Cultivar denomination: 'DUEINFINITYWI'.

BACKGROUND OF THE INVENTION

The present invention relates to a new and distinct cultivar of Poinsettia plant, botanically known as *Euphorbia pulcherrima* Willd., and hereinafter referred to by the name 'Dueinfinitywi'.

The new Poinsettia is a naturally-occurring whole plant mutation of a proprietary selection of *Euphorbia pulcherrima* Willd. identified as code number W040, not patented. The cultivar Dueinfinitywi was discovered and selected by the Inventor as a flowering plant within a population of plants of the parent selection in a controlled greenhouse environment in Rheinberg, Germany in December, 2005.

Asexual reproduction of the new Poinsettia by terminal vegetative cuttings in a controlled environment in Rheinberg, Germany since December, 2005, has shown that the unique features of this new Poinsettia are stable and reproduced true to type in successive generations of asexual reproduction.

SUMMARY OF THE INVENTION

The cultivar Dueinfinitywi has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Dueinfinitywi'. These characteristics in combination distinguish 'Dueinfinitywi' as a new and distinct cultivar of Poinsettia:

1. Upright and outwardly spreading plant habit.
2. Freely branching habit.

3. Early flowering habit.
4. Inflorescences with light yellow-colored flower bracts.
5. Excellent post-production longevity.

In side-by-side comparisons conducted in Rheinberg, Germany, plants of the new Poinsettia differed primarily from plants of the parent selection in flower bract coloration as plants of the parent selection had red-colored flower bracts.

Plants of the new Poinsettia can be compared to plants of the Poinsettia cultivar Elegance White, not patented. In side-by-side comparisons conducted in Rheinberg, Germany, plants of the new Poinsettia differed primarily from plants of the cultivar Elegance White in flower bract color as plants of the new Poinsettia had lighter yellow-colored flowers bracts than plants of the cultivar Elegance White. In addition, plants of the new Poinsettia were more upright in plant habit than plants of the cultivar Elegance White.

BRIEF DESCRIPTION OF THE PHOTOGRAPH

The accompanying photograph illustrates the overall appearance of the new Poinsettia. The photograph shows the colors as true as it is reasonably possible to obtain in colored reproductions of this type. Colors in the photograph may differ slightly from the color values cited in the detailed botanical description which accurately describe the colors of the new Poinsettia. The photograph comprises a side perspective view of a typical flowering plant of 'Dueinfinitywi' grown in a container.

DETAILED BOTANICAL DESCRIPTION

In the following description, color references are made to The Royal Horticultural Society Colour Chart, 1995 Edition, except where general terms of ordinary dictionary significance are used. The aforementioned photograph and following observations and measurements describe plants grown in Rheinberg, Germany during the winter in a glass-covered greenhouse and under conditions and practices which approximate those generally used in commercial Poinsettia production. During the production of the plants, day and night temperatures averaged 22° C. and light levels were about 4,500 lux. Measurements and numerical values represent averages for typical flowering plants. Single plants were grown in 13-cm containers and were pinched one time about five weeks after planting the cuttings. Plants were about 16 weeks old when the photograph and the detailed description were taken.

Botanical classification: *Euphorbia pulcherrima* cultivar Dueinfinitywi.

Parentage: Naturally-occurring whole plant mutation of a proprietary selection of *Euphorbia pulcherrima* Willd. identified as code number W040, not patented.

Propagation:

*Type.*—Terminal vegetative cuttings.

*Time to initiate roots, summer.*—About nine days at 22° C.

*Time to initiate roots, winter.*—About 13 days at 22° C.

*Time to produce a rooted young plant, summer.*—About three weeks at 22° C.

*Time to produce a rooted young plant, winter.*—About four weeks at 22° C.

*Root description.*—Fibrous, fleshy; white in color.

*Rooting habit.*—Freely branching; dense.

Plant description:

*Plant habit and form.*—Upright and outwardly spreading plant habit; inverted triangle. Inflorescences positioned above the foliar plane. Moderately vigorous growth habit.

*Plant height.*—About 21 cm.

*Plant diameter or spread.*—About 38 cm.

*Lateral branch description.*—Quantity: Freely branching habit, about six to seven lateral branches develop after pinching. Length: About 19 cm. Diameter: About 6 mm. Internode length: About 1 cm. Strength: Strong. Texture: Smooth, glabrous. Color: 137A.

*Foliage description.*—Arrangement: Alternate, simple. Length: About 9.8 cm. Width: About 7.3 cm. Shape: Ovate. Apex: Apiculate. Base: Obtuse. Margin: Lobed; dentate. Venation pattern: Pinnate. Texture, upper and lower surfaces: Smooth, glabrous. Color: Developing foliage, upper surface: 141B. Developing foliage, lower surface: 137B. Fully expanded foliage, upper surface: 139A; venation, 144B. Fully expanded foliage, lower surface: 138A; venation, 144B. Petiole: Length: About 4.8 cm. Diameter: About 2.8 mm. Texture, upper and lower surfaces: Smooth, glabrous. Color, upper and lower surfaces: 144B.

*Inflorescence description.*—Inflorescence type and habit: Inflorescences are compound corymbs of cyathia with colored flower bracts subtending the cyathia. One inflorescence per lateral branch. Flowers are not fragrant. Flowers persistent. Inflorescences positioned above the foliage. Natural flowering season: Autumn/winter; inflorescence initiation and development is induced under long nyctoperiod conditions. Early flowering, response time is about eight weeks. Post-production longevity: Excellent post-production longevity; plants of the new Poinsettia maintain good substance and bract color for about eight weeks under interior conditions. Inflorescence size: Diameter: About 20 cm. Height (depth): About 4 cm. Flower bracts: Quantity per inflorescence: About 14. Length: About 10.3 cm. Width: About 7 cm. Shape: Ovate; slightly lobed. Apex: Apiculate. Base: Obtuse. Margin: Entire; slightly lobed. Texture, upper and lower surfaces: Glabrous; rugose. Venation pattern: Pinnate. Color: Developing or transitional bracts, upper and lower surfaces: 1C. Fully developed bracts, upper and lower surfaces: 2D. Venation, upper and lower surfaces: Similar to flower bract color. Bract petiole: Length: About 1.7 cm. Diameter: About 2.2 mm. Texture, upper and lower surfaces: Smooth, glabrous. Color, upper and lower surfaces: 144B. Cyathia: Quantity per corymb: About 15. Diameter of cyathia cluster: About 2.5 cm. Length: About 7 mm. Width: About 6 mm. Shape: Ovoid. Color, immature: 144B. Color, mature: 144A. Nectaries: Quantity per cyathium: About one or two. Diameter: About 5 mm. Color: 14A. Peduncles: Length: About 4 mm. Diameter: About 2.5 mm. Strength: Strong to moderately strong. Texture: Smooth, glabrous. Color: 144B.

*Reproductive organs.*—Stamens: Quantity per cyathium: About 30. Anther shape: Oval. Anther length: About 1 mm. Anther color: 9B. Amount of pollen: Abundant. Pollen color: 14A. Pistils: Quantity per cyathium: One. Pistil length: About 1 cm. Style length: About 2 mm. Style color: 144B. Stigma shape: Crested. Stigma color: 144C. Ovary color: 144A.

*Seed/fruit.*—Seed and fruit production has not been observed.

Disease/pest resistance: Plants of the new Poinsettia have been shown to be resistant to Botrytis. Plants of the new Poinsettia have not been shown to be resistant to pests and other pathogens common to Poinsettias.

Temperature tolerance: Plants of the new Poinsettia have been observed to tolerate temperatures ranging from about 12° C. to about 40° C.

It is claimed:

1. A new and distinct Poinsettia plant named 'Dueinfinitywi' as illustrated and described.

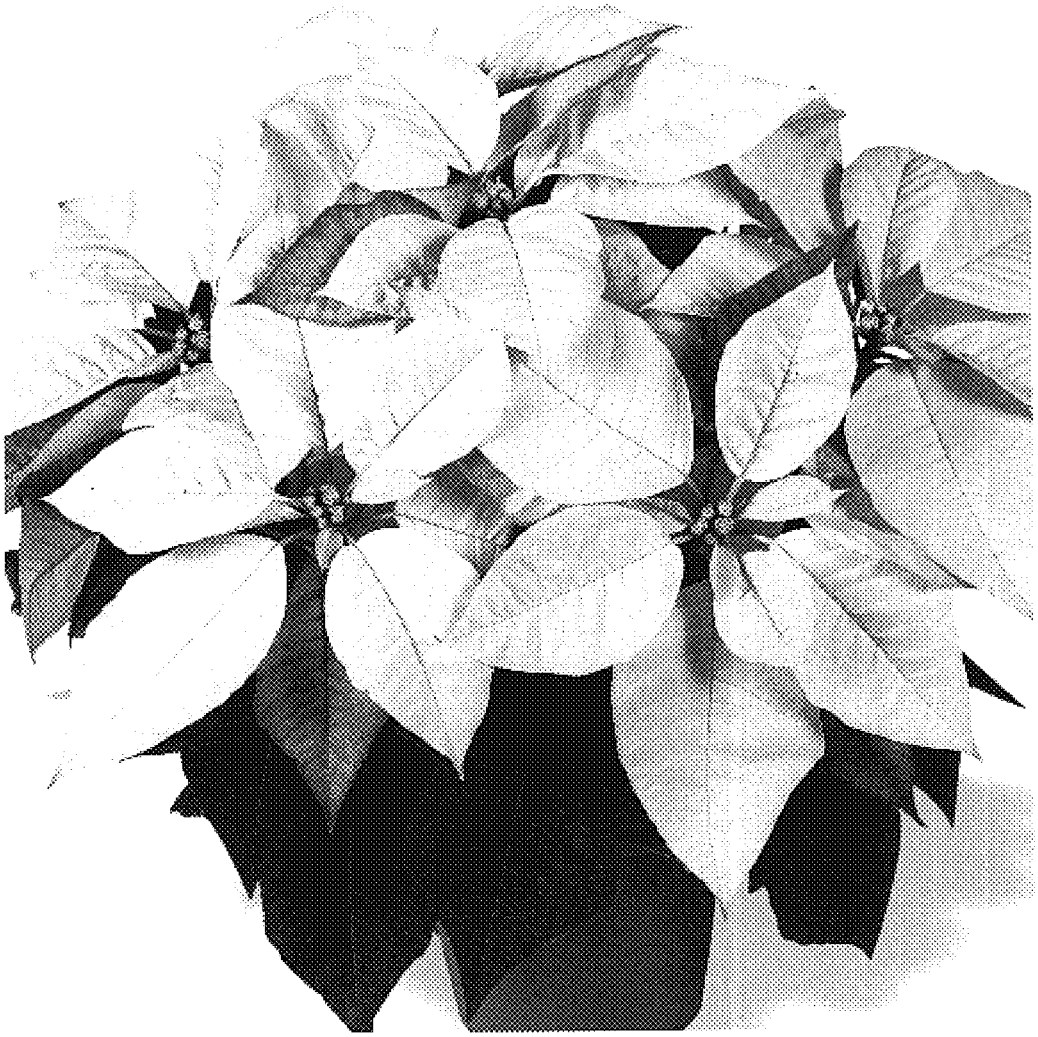

* * * * *